United States Patent
Morimoto et al.

(10) Patent No.: US 6,342,590 B1
(45) Date of Patent: Jan. 29, 2002

(54) ERYTHROMYCIN A DERIVATIVES AND METHOD FOR PREPARING SAME

(75) Inventors: Shigeo Morimoto; Takashi Adachi, both of Saitama-ken; Tohru Matsunaga; Masato Kashimura, both of Ageo; Yoshiaki Watanabe, Kodaira; Kaoru Sota, Tokorozawa, all of (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 07/869,111

(22) Filed: Apr. 14, 1992

Related U.S. Application Data

(63) Continuation of application No. 07/094,888, filed on Sep. 10, 1987, now abandoned.

(30) Foreign Application Priority Data

Sep. 18, 1986 (JP) ............................................. 2-220315

(51) Int. Cl.$^7$ .................................................. C07H 1/00
(52) U.S. Cl. ........................................ 536/7.4; 536/18.5
(58) Field of Search ..................... 536/7.2, 7.3, 7.5, 536/18.5; 514/29

(56) References Cited

U.S. PATENT DOCUMENTS

| | | | | |
|---|---|---|---|---|
| 4,640,910 A | * | 2/1987 | Fausl et al. ..................... | 514/29 |
| 4,670,549 A | * | 6/1987 | Moromoto et al. .......... | 536/7.4 |

FOREIGN PATENT DOCUMENTS

| | | |
|---|---|---|
| EP | 0063489 | 10/1982 |
| EP | 0158467 | * 10/1985 |
| EP | 0201166 | 11/1986 |
| EP | 0222353 | 5/1987 |

OTHER PUBLICATIONS

Kirk–Othmer, Encyclopedia of Chemical Technology, 3$^{rd}$ ed, vol. 20, published 1982 pp 964–965.*
Kirk–Othmer, Encyclopedia of Chemical Technology, Third Ed., (New York, John Wiley & Sons), 20, pp. 964–965 (1982).*
Kirk–Othmer, Encyclopedia of Chemical Technology, Third Ed., (New York, John Wiley & Sons), 20, pp. 964–965 (1982).*

* cited by examiner

Primary Examiner—Elli Peselev
(74) Attorney, Agent, or Firm—Lorusso & Loud

(57) ABSTRACT

Erythromycin A derivatives represented by the general formula

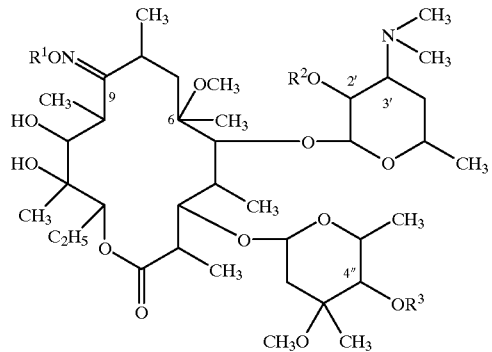

wherein $R^1$ is a 2-alkenyl group having 3 to 15 carbon atoms, an arylmethyl group, or an arylmethyl group substituted by 1 to 3 of a halogen atom, an alkoxy group 1 to 4 carbon atoms, a nitro group or an alkoxycarbonyl group having 2 to 6 carbon atoms, $R^2$ is a substituted silyl group and $R^3$ is a hydrogen atom or $R^2$, are disclosed. These compounds are useful as intermediates of the anti-bacterial agents.

1 Claim, No Drawings

ERYTHROMYCIN A DERIVATIVES AND METHOD FOR PREPARING SAME

This application is a continuation, of application Ser. No. 07/094,888, filed Sep. 10, 1987 now abandoned.

BACKGROUND OF THE INVENTION

1. Field of the Invention

The present invention relates to erythromycin A derivatives and the method for the preparation of the same.

2. Description of the Prior Art

6-O-Methylerythromycins are useful as anti-bacterial agents or intermediates for synthesis of the antibacterial agents. For example, 6-O-methylerythromycin A is not only stable under the acidic conditions but also has a strong antibacterial activity when compared with erythromycin A. Especially, this compound shows an excellent effect for treatment of infections by oral administration, and therefore it is a useful antibacterial agent.

There are known in the past some methods for methylating the hydroxy group at the 6-position of the erythromycin A derivatives, for example, (1) a method which comprises substituting the hydrogen atom of the hydroxy group at the 2'-position and the methyl group of the dimethylamino group at the 3'-position of the erythromycin A derivatives by benzyloxycarbonyl groups, and then methylating the resulting compound (U.S. Pat. No. 4,331,803), and (2) a method which comprises converting erythromycin A derivatives having the protected hydroxy group at the 2'-position and/or the protected dimethylamino group at the 3'-position into the various kind of the substituted oxime derivative, and then methylating the substituted derivatives (European Patent 158,467).

However, since erythromycin A has many hydroxy groups, there are obtained various kind of erythromycin A derivatives which are methylated at hydroxy groups at any other than the 6-position as the by-products by the method of item (1). Accordingly, this method requires the complicated procedure for purification of the 6-O-methylerythromycin A derivatives, and has drawback of causing low yield of said derivatives. Although it is possible to methylate selectively the 6-hydroxy group by the method of item (2), when the erythromycin A 9-oxime derivative whose 2'-hydroxy group only is protected is methylated, the 3'-dimethylamino group is changed to a methyl quaternary salt under ordinary methylation conditions. Furthermore it is difficult to return the salt to a dimethylamino group, accordingly, it is necessary to protect both of the 2'-hydroxy group and 3'-dimethylamino group for the practical preparation method.

SUMMARY OF THE INVENTION

As a result of the various researches to solve the drawbacks of the above known methods, the present inventors have found the fact that erythromycin A derivative whose 2'-hydroxy group is protected with the substituted silyl groups is not quaternarized at the adjacent 3'-dimethylamino group even under ordinary methylation conditions, and the present invention has been completed.

DETAILED DESCRIPTION OF THE INVENTION

An object of the present invention is to provide 6-O-methylerythromycin A derivatives represented by the general formula

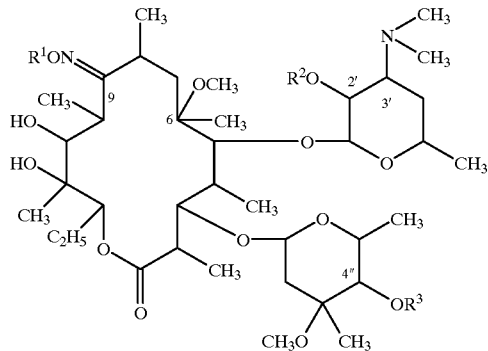

wherein $R^1$ is a 2-alkenyl group having 3 to 15 carbon atoms, an arylmethyl group, or an arylmethyl group substituted by 1 to 3 of a halogen atom, an alkoxy group having 1 to 4 carbon atoms, a nitro group or an alkoxycarbonyl group having 2 to 6 carbon atoms, $R^2$ is a substituted silyl group of formula $—SiR^4R^5R^6$ (wherein $R^4$, $R^5$ and $R^6$ are the same or different, and each is a hydrogen atom, an alkyl group having 1 to 15 carbon atoms, a phenyl substituted alkyl group in which the alkyl moiety has 1 to 3 carbon atoms, a phenyl group, a cycloalkyl group having 5 to 7 carbon atoms or an alkenyl group having 2 to 5 carbon atoms, with the proviso that at least one of $R^4$, $R^5$ and $R^6$ is other than hydrogen atom) and $R^3$ is a hydrogen atom or $R^2$.

Another object of the present invention is to provide erythromycin A derivatives represented by the general formula

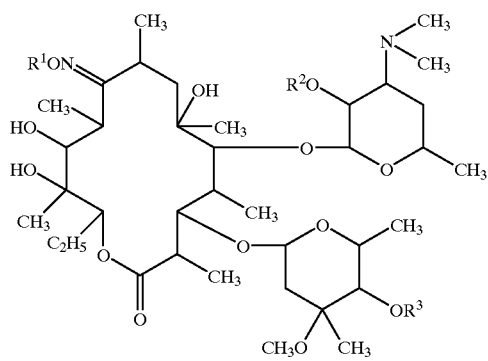

wherein $R^1$, $R^2$ and $R^3$ are as defined above.

Still another object of the present invention is to provide a method for preparing 6-O-methylerythromycin A derivatives of formula I which comprises reacting, in any desired sequence, erythromycin A 9-oxime with a compound of formula $R^1—X$ (wherein $R^1$ is as defined above, and X is a halogen atom) and with a substituted silylating agent having $R^2$ group to give a compound of formula II, and then reacting the compound of formula II with a methylating agent.

In the present invention, the terms "alkyl", "alkoxy" and "alkenyl" used alone or as combined with the other group mean those whose carbon chain may be linear or branched. The term "arylmethyl group" means a benzyl group, a benzhydryl group, a trityl group or a naphthylmethyl group. Examples of the substituted arylmethyl group are a p-methoxybenzyl group, a p-chlorobenzyl group, a m-chlorobenzyl group, an o-chlorobenzyl group, a 2,4- dichlorobenzyl group, a p-bromobenzyl group, a m-nitrobenzyl group, a p-nitrobenzyl group and the like. Examples of 2-alkenyl group for $R^1$ are an allyl group, a methallyl group, a crotyl group, a prenyl group, a 2-pentenyl group, a 2-ethyl-2-butenyl group, a geranyl group, a neryl group and the like. The term "halogen atom" refers to a chlorine, a bromine, an iodine atom and the like. Examples of the substituted silyl group are a trimethylsilyl group, a triethylsilyl group, an isopropyldimethylsilyl group, a tert-butyldimethylsilyl group, a (triphenylmethyl)dimethylsilyl group, a tert-butyldiphenylsilyl group, a diphenylmethylsilyl group, a diphenylvinylsilyl group, a methyldiisopropylsilyl group, a tribenzylsilyl group, a tri(p-xyryl)silyl group, a triphenylsilyl group, a diphenylsilyl group, a dimethyloctadecylsilyl group and the like.

The present invention is illustrated below in more detail. At first, etherification of erythyromycin A 9-oxime with a compound of formula $R^1$—X is carried out according to the known method per se, for example, the method described in European Patent No. 158,467 to give a compound of formula

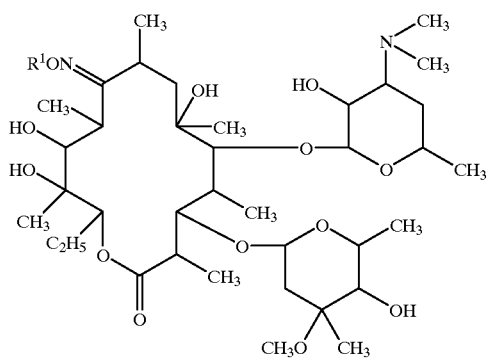

III wherein $R^1$ is as defined above.

The reaction of the compound of formula III with the silylating agent is carried out in a solvent in the presence of a base at 0° C. to the reflux temperature of the solvent, preferably at room temperature with stirring. Examples of the silylating agent used are chlorosilanes such as trimethylchlorosilane, tert-butyldimethychlorosilane and the like; silylamines such as 1,1,1,3,3,3-hexamethyldisilazane, trimethylsilylimidazole, dimethylaminotrimethylsilane and the like; bis(trimethylsilyl)acetamide, trimethylsilyldiphenylurea, bis(trimethylsilyl)urea and the like. The amount of the silylating agent used is 1 to 10 equivalents, preferably 1 to 5 equivalents relative to the compound of formula III.

Examples of the solvent used in the reaction are acetone, tetrahydrofuran, N,N-dimethylformamide, dimethyl sulfoxide, dioxane, 1,2-dimethoxyethane, dichloromethane, chloroform and the like. Examples of the base are inorganic bases such as sodium hydroxide, potassium hydroxide, potassium carbonate, sodium bicarbonate, potassium bicarbonate and the like; and organic bases such as trimethylamine, triethylamine, pyridine, 1,8-diaza-bicyclo [5,4,0]unde-7-cene, imidazole and the like.

Although difference of the silylation at the 2-position only between both of the 2'- and 4"-positions of the compound of formula III depends on the reaction conditions, it is preferable to use a chlorosilane for the silylation at the 2-position only, and it is preferable to use both a chlorosilane and a silylamine or 1,1,1,3,3,3-hexamethyldisilazane for the silylation at the 2'- and 4"-positions.

Alternatively, the compound of formula II can be obtained by etherification after silylation of erythromycin A 9-oxime. Namely, erythromycin A 9-oxime is reacted with the silylating agent under the same silylation conditions as described above, and then the resulting compound is reacted with the compound of formula $R^1$—X under the same etherification conditions as described above to give the compound of formula II.

The reaction of the compound of formula II with the methylating agent for preparing the compound I can be carried out in a solvent in the presence of a base at −15° C. to room temperature, preferably at 0° C. to room temperature with stirring. Examples of the methylating agent are methyl bromide, methyl iodide, dimethyl sulfate, methyl p-toluenesulfonate, methyl methanesulfonate and the like. It is sufficient to use 1–3 molar equivalents of the methylating agent relative to the compound of formula II. Examples of the solvents used are polar aprotic solvent such as N,N-dimethylformamide, dimethyl sulfoxide, N-methyl-2-pyrrolidone, hexamethylphosphoric triamide, a mixture thereof or a mixture of one of these solvents and a solvent such as tetrahydrofuran, 1,2-dimethoxyethane, acetonitrile, ethyl acetate or the like. Examples of the base are sodium hydroxide, potassium hydroxide, sodium hydride, potassium t-butoxide, potassium hydride and the like. The amount of the base used is usually 1–2 molar equivalents relative to the compound of formula II.

In order to prevent the quaternarization of the 3'-dimethylamino group when the compound of formula II is methylated, it is essential to protect the 2'-hydroxy group with the substituted silyl ether, but not necessarily essential to etherify the 4"-hydroxy group with the substituted silyl group.

The compound of formula II may be used after isolation or without isolation for reacting with the methylating agent.

Although erythromycin A 9-oxime derivatives of the present invention exist in two isomers (syn- and anti-forms), for the purpose of the present invention, these compounds may exist in either of the isomers and in a mixture thereof.

In the method for preparing the 6-O-methylerythromycin A derivatives of the present invention, it is not necessary to protect the 3'-dimethylamino group, therefore, it is not necessary to carry out the 3'-N-methylation, either.

The methylation of the hydroxy group at the 6-position of the present invention has good selectivity as well as the prior art method. Furthermore, the substituted silyl groups used for the protection of the hydroxy groups at the 2'- and 4"-positions can be easily eliminated.

Therefore, the present invention can provide 6-O-methylerythromycin A in high yield and economically. Namely, the compound of formula I can be led to 6-O-methylerythromycin A, for example, by the following method.

The elimination of the substituted silyl groups ($R^2$ and $R^3$) at the 2'- and 41-positions of the compound of formula I can be carried out easily by treatment with an acid (e.g., formic acid) in an alcohol or with tetrabutyl ammoniumfluoride in tetrahydrofuran.

The elimination of $R^1$ group of the resulting compound can be carried out by homogeneous or heterogeneous hydrogenolysis known per se. For example, this reaction may be carried out in an alcoholic solvent (e.g., methanol, ethanol and the like) in the presence of a catalyst such as palladium black or palladium carbon under a hydrogen atomosphere with stirring. The addition of formic acid, acetic acid or the like is convenient for the progress of the reaction.

This reaction can also be carried out easily in the presence of a suitable hydrogen source (e.g., ammonium formate, sodium formate, and a mixture of these formates and formic acid) and a catalyst (e.g., palladium carbon, palladium black and the like) in an organic solvent (e.g., methanol, ethanol, N,N-dimethylformamide and the like) with stirring at room temperature to 70° C.

Furthermore, this reaction may be carried out by using a platinum group compound and a ligand as a catalyst. Examples of the platinum group compound are the salts or complexes of ruthenium, rhodium, palladium and platinum, and examples of the ligand are phosphor compounds such as triphenylphosphine, tri-n-butylphosphine, triethylphosphite, 1,2-ethylene(diphenyl)phosphine and the like. Usually, mixture of palladium acetate and triphenylphosphine may be used. This reaction can be carried out in the presence of formic acid or a salt thereof. Examples of the salt of formic acid are ammonium salts thereof such as ammonium formate, trimethylammonium formate, triethylammonium formate and the like, and alkali metal salts thereof such as sodium formate, potassium formate and the like.

The elimination procedure of $R^2$ and $R^3$ and that of $R^1$ may be carried out in the reverse order without any trouble.

6-O-Methylerythromycin A 9-oxime thus obtained can be converted easily to 6-O-methylerythromycin A by deoximation using sodium hydrogen sulfite, titanium trichloride-ammonium acetate, sodium nitrite-hydrochloric acid, sodium hydrosulfite ($Na_2S_2O_4$) and the like.

Next, the present invention will be concretely illustrated by Examples which show the method for preparing the compound of formula I and Referential Examples which show the method for preparing 6-O-methylerythromycin A.

EXAMPLE 1

Preparation of 2'-O-trimethylsilylerythromycin A 9-(O-benzyloxime)

To a solution of 3.36 g of erythromycin A 9-(O-benzyloxime) and 0.7 ml of triethylamine in 30 ml of N,N-dimethylformamide was added dropwise at room temperature 0.7 ml of trimethylchlorosilane, and the mixture was stirred for 10 minutes. To the reaction solution was added isopropyl ether, and the mixture was washed with, in turn, water and a saturated aqueous sodium chloride solution and dried over anhydrous magnesium sulfate. The solvent was evaporated and the resulting crude product was recrystallized from isopropyl ether to give 1.35 g of the title compound as colorless needles.

m.p. 104–106° C.

Mass(FAB); m/z: 911(MH$^+$)

PMR(CDCl$_3$)

δ (ppm)=0.11(2'-O-TMS), 2.23[3'N(CH$_3$)$_2$], 3.33(3"-OCH$_3$)

CMR(CDCl$_3$)

δ (ppm)=1.0(2'-O-TMS), 41.0[3'-N(CH$_3$)$_2$], 49.5(3"-OCH$_3$)

(TMS as used above and hereinafter is a trimethylsilyl group)

EXAMPLE 2

Preparation of 2',4"-O-bis(trimethylsilyl) erythromycin A 9-(O-benzyloxime)

To a solution of 2.24 g of trimethylsilylimidazole and 1.74 g of trimethylchlorosilane in 20 ml of dry dichloromethane was added at once at room temperature a solution of 6.72 g of erythromycin A 9-(O-benzyloxime) in 40 ml of dichloromethane, and the mixture was stirred at room temperature for 10 minutes. Chloroform was added, and the mixture was washed with, in turn, water and a saturated aqueous sodium chloride solution and dried over anhydrous magnesium sulfate. The solvent was evaporated and the resulting crude product was recrystallized from acetone-water to give 5.27 g of the title compound as colorless needles.

m.p. 97–100° C.

Mass(FAB); m/z: 983(MH$^+$)

PMR(CDCl$_3$)

δ (ppm)=0.09(2'-O-TMS), 0.15(4"-O-TMS), 2.22[3'-N(CH$_3$)$_2$], 3.31(3"-OCH$_3$)

CMR(CDCl$_3$);

δ (ppm) =0.9(4"-O-TMS), 1.0(2'-O-TMS), 41.0[3'-N(CH$_3$)$_2$], 49.7(3"-OCH$_3$)

EXAMPLE 3

Preparation of 2'-O-trimethylsilyl-6-O-methylerythromycin A 9-(O-benzyloxime)

To a solution of 2.28 g of 2'-O-trimethylsilylerythromycin A 9-(O-benzyloxime) in 20 ml of a mixture of dimethyl sulfoxide and tetrahydrofuran (1:1) were added 0.38 ml methyl iodide and 280 mg of 85% potassium hydroxide powder, and the mixture was stirred at room temperature for 2 hours. To the reaction solution was added ethyl acetate, and the mixture was washed with, in turn, water and a saturated aqueous sodium chloride solution, and dried over anhydrous magnesium sulfate. The solvent was evaporated to give 2.32 g of the glassy title compound.

Mass(FAB); m/z: 925(MH$^+$)

PMR(CDCl$_3$)

δ (ppm)=0.09(2'-O-TMS), 2.23[3'-N(CH$_3$)$_2$], 3.03(6-OCH$_3$), 3.34(3"-OCH$_3$)

EXAMPLE 4

Preparation of 2,4"-O-bis(trimethylsilyl)-6-O-methylerythromycin A 9-(O-benzyloxime)

Treating 3.93 g of 2',4"-O-bis(trimethylsilyl) erythromycin A 9-(O-benzyloxime) according to the procedure similar to that of Example 3, there was obtained 3.89 g of the glassy title compound.

m.p. 115–116° C. (recrystallized from methanol)

Mass(FAB); m/z: 997(MH$^+$)

PMR(CDCl$_3$)

δ (ppm)=0.09(2'-O-TMS), 0.15(4"-O-TMS), 2.21[3'-N(CH$_3$)$_2$], 3.03(6-OCH$_3$), 3.32(3"-OCH$_3$)

CMR(CDCl$_3$)

δ (ppm)=0.9(4"-O-TMS), 1.1(2'-OCH$_3$), 41.0[3'-N(CH$_3$)$_2$], 49.7(3"-OCH$_3$), 50.7(6-OCH$_3$)

EXAMPLE 5

Preparation of 2'-O-trimethylsilylerythromycin A 9-(O-allyloxime)

Treating 1 g of erythromycin A 9-(O-allyloxime) according to the procedure similar to that of Example 1, there was obtained the crude product, which was then purified by alumina column chromatography (eluent; acetone/n-hexane=1/10–1/5) to give 0.35 g of the glassy title compound.

m.p. 93–96° C. (recrystallized from n-hexane)
Mass(EI); m/z: 860(M+)
PMR(CDCl$_3$)
δ (ppm)=0.11(2'-O-TMS), 2.23[3'-N(CH$_3$)$_2$], 3.32(3"-OCH$_3$)
CMR(CDCl$_3$)
δ (ppm)=1.0(2'-O-TMS), 41.0[3'-N(CH$_3$)$_2$], 49.5(3"-OCH$_3$)

EXAMPLE 6

Preparation of 2',4"-O-bis(trimethylsilyl) erythromycin A 9-(O-allyloxime)

Allowing to react 1 g of erythromycin A 9-(O-allyloxime) according to the procedure similar to that of Example 2, and then 100 ml of n-hexane was added to the reaction solution. The insoluble was filtered off, and the filtrate was concentrated. The residue was purified by silica gel column chromatography (eluent; acetone/n-hexane/triethylamine=1/10/0.1) to give 0.70 g of the glassy title compound.

m.p. 85–89° C. (recrystallized from acetone)
Mass(EI); m/z: 932(M+)
PMR(CDCl$_3$)
δ (ppm)=0.10(2'-O-TMS), 0.14(4"-O-TMS), 2.22[3'-N(CH$_3$)$_2$], 3.31(3"-OCH$_3$)

EXAMPLE 7

Preparation of 2'-O-trimethylsilyl-6-O-methylerythromycin A 9-(O-allyloxime)

To a solution of 4 g of erythromycin A 9-(O-allyloxime) and 1.4 ml of triethylamine in 20 ml of N,N-dimethylformamide was added dropwise at room temperature 1.35 ml of trimethylchlorosilane, and the mixture was stirred for 20 minutes. 100 ml of water was added, and the mixture was extracted with ethyl ether. The organic layer was washed with a saturated aqueous sodium chloride solution and dried over anhydrous magnesium sulfate. The solvent was evaporated to give 3.86 g of the crude product of 2'-O-trimethylsilylerythromycin A 9-(O-allyloxime).

To a solution of the above compound in 30 ml of a mixture of dimethyl sulfoxide and tetrahydrofuran (1:1), were added under ice-cooling 0.42 ml of methyl iodide and then 357 mg of 85% sodium hydroxide powder, and the mixture was stirred for 1.5 hours. After completion of the reaction, 0.5 ml of 50% aqueous dimethylamine solution was added, and the mixture was stirred for an hour. 100 ml of water was added, and the mixture was extracted with ethyl acetate. The organic layer was washed with a saturated aqueous sodium chloride solution and dried over anhydrous magnesium sulfate. The solvent was evaporated, and the residue was purified by silica gel column chromatography (eluent; acetone/n-hexane/triethylamine=1/5/0.1) to give 1.45 g of the glassy title compound.

m.p. 155–158° C. (recrystallized from n-hexane)
Mass(EI); m/z: 874(M+)
PMR(CDCl$_3$)
δ (ppm)=0.10(2'-O-TMS), 2.22[3'-N(CH$_3$)$_2$], 3.08(6-OCH$_3$), 3.33(3"-OCH$_3$)
CMR(CDCl$_3$)
δ (ppm)=1.1(2'-O-TMS), 41.0[3'-N(CH$_3$)$_2$], 49.4(3"-OCH$_3$), 50.9(6-OCH$_3$)

EXAMPLE 8

Preparation of 2',4"-O-bis(trimethylsily)-6-O-methylerythromycin A 9-(O-allyloxime)

To a solution of 3.51 ml of trimethylsilylimidazole and 3.04 ml of trimethylchlorosilane in 25 ml of dry dichloromethane was added at once at room temperature a solution of 9.5 g of erythromycin A 9-(O-allyloxime) in 125 ml of dichloromethane, and the mixture was stirred at room temperature for 10 minutes. To the reaction solution was added 400 ml of n-hexane, the insoluble was filtered off, and the filtrate was concentrated. To the residue was added 200 ml of n-hexane, the resulting insoluble was filtered off, and the filtrate was concentrated. To a solution of the residue in 75 ml of a mixture of dimethyl sulfoxide and tetrahydrofuran (1:1) were added under ice-cooling 1 ml of methyl iodide and then 854 mg of 85% potassium hydroxide powder, and the mixture was stirred for 1.5 hours. After completion of the reaction, the treatment similar to that of Example 7 gave 10.2 g of the title compound.

m.p. 96–101° C. (recrystallized from acetone-water)
Mass(EI); m/z: 946(M+)
PMR(CDCl$_3$)
δ (ppm)=0.09(2'-O-TMS), 0.15(4"-O-TMS), 2.22[3'-N(CH$_3$)$_2$], 3.09(6-OCH$_3$), 3.32(3"-OCH$_3$)
CMR(CDCl$_3$)
δ (ppm)=0.9(6-O-TMS), 1.1(2'-O-TMS), 41.0[3'-N(CH$_3$)$_2$], 49.7(3"-OCH$_3$), 50.9(6-OCH$_3$)

EXAMPLE 9

Preparation of 2',4"-O-bis(trimethylsilyl)-6-O-methylerythromycin A 9-(O-allyloxime) from erythromycin A 9-oxime To a solution of 10 g of erythromycin A 9-oxime in 75 ml of tetrahydrofuran were added 1.25 ml of allyl bromide and 970 mg of 85% potassium hydroxide powder, and the mixture was stirred at room temperature for 2 hours. To the reaction solution was added 1 ml of 50% aqueous dimethylamine solution, and the mixture was stirred for 30 minutes, poured into a mixture of methanol and water (50 ml: 200 ml) and stirred under ice-cooling for 30 minutes. The resulting precipitate was collected by filtration, washed with water, dissolved in chloroform and dried over anhydrous magnesium sulfate. The solvent was evaporated to give 9.7 g of crude erythromycin A 9-(O-allyloxime).

To a solution of 3.58 ml of trimethylsilylimidazole and 3.10 ml of trimethylchlorosilane in 25 ml of dry dichloromethane was added at once at room temperature a solution of 9.7 g of erythromycin A 9-(O-allyloxime), obtained above, in 125 ml of dichloromethane, and the mixture was stirred at room temperature for 10 minutes. To the reaction solution was added 200 ml of n-hexane, the resulting insoluble was filtered off, and the filtrate was concentrated. To the residue was added once more 200 ml of n-hexane, the insoluble was filtered off, and the filtrate was concentrated to give 10 g of crude 2',4"-O-bis(trimethylsilyl) erythromycin A 9-(O-allyloxime).

To a solution of 10 g of crude 2',4"-O-bis(trimethylsilyl) erythromycin A 9-(O-allyloxime), obtained above, in 75 ml of a mixture of dimethyl sulfoxide and tetrahydrofuran (1:1) were added 1 ml of methyl iodide and then 837 mg of 85% potassium hydroxide powder, and the mixture was stirred under ice-cooling for 1.5 hours. After completion of the reaction, 1 ml of 50% aqueous dimethylamine solution was added, and the mixture was stirred at room temperature for an hour. 200 ml of water was added, and the mixture was extracted with ethyl acetate. The organic layer was washed with a saturated aqueous sodium chloride solution and then dried over anhydrous magnesium sulfate. The solvent was evaporated to give 10.3 g of crude 2',4"-O-bis(trimethylsilyl)-6-O-methylerythromycin A 9-(O- allyloxime). Purification similar to that of Example 8 gave the title compound, which was identical with the compound obtained in Example 8 in terms of melting point, and spectra of mass, PMR and CMR.

EXAMPLE 10

Preparation of 2',4"-O-bis(trimethylsilyl) erythromycin A 9-(O-benzyloxime) from erythromycin A 9-oxime To a solution of 3.79 g of erythromycin 9-oxime and 0.75 ml of benzyl chloride in 30 ml of N,N-dimethylformamide was added under ice-cooling 0.24 g of sodium hydride (60%). After stirring for 2 hours, 2.5 ml of 1,1,1,3,3,3-hexamethyldisilazane and 0.99 g of pyridine hydrochloride were added, and the mixture was stirred for a further 6 hours. After being allowed to stand overnight, the reaction solution was poured into water, extracted with ethyl acetate. The organic layer was washed with water and dried over anhydrous magnesium sulfate. The solvent was evaporated and the resulting crude product was recrystallized from an aqueous acetone to give 3.0 g of the title compound, which was identical with the compound obtained in Example 2 in terms of melting point and spectra of mass and PMR.

EXAMPLE 11

Preparation of 2',4"-O-bis(trimethylsilyl)-6-O-methylerythromycin A 9-[O-(o-chlorobenzyl)oxime]

(1) To a solution of 90 g of erythromycin A 9-oxime in 500 ml of N,N-dimethylformamide were added 23.6 g of o-chlorobenzyl chloride and 9.7 g of 85% potassium hydroxide powder, and the mixture was stirred under ice-cooling for 30 minutes. After completion of the reaction, the mixture was extracted with ethyl acetate, washed with, in turn, water and a saturated aqueous sodium chloride solution and dried over anhydrous magnesium sulfate. The solvent was evaporated under reduced pressure to give 98 g of erythromycin A 9-[O-(o-chlorobenzyl)oxime].
m.p. 114–117° C. (recrystallized from n-hexane)
(2) To a solution of 8.7 g of the above compound in 80 ml of ethyl acetate was added a solution of 2.53 ml of trimethylchlorosilane and 2.8 g of trimethylsilylimidazole in 10 ml of ethyl acetate, and the mixture was stirred at room temperature for an hour. To the mixture was added n-hexane, and the mixture was washed with, in turn, water and a saturated aqueous sodium chloride solution and dried over anhydrous magnesium sulfate. The solvent was evaporated to give 9.78 g of glassy 2',4"-O-bis(trimethylsilyl)erythromycin A 9-[O-(o-chlorobenzyl)oxime].
Mass(EI); m/z: 1016(M$^+$)
PMR(CDCl$_3$)
δ (ppm)=0.10(2'-O-TMS), 0.15(4"-O-TMS), 2.23[3'-N(CH$_3$)$_2$], 3.30(3"-OCH$_3$)
(3) To a solution of 5.09 g of 2',4"-O-bis(trimethylsilyl) erythromycin A 9-[O-(o-chlorobenzyl)oxime] in 100 ml of a mixture of dimethyl sulfoxide and tetrahydrofuran (1:1) were added 0.41 ml of methyl iodide and then 360 mg of 85% potassium hydroxide powder, and then the mixture was stirred under ice-cooling for 1.5 hours. To the reaction solution was added 2 ml of 50% aqueous dimethyl amine solution, and the stirring was continued for 30 minutes. Thereafter, to the mixture was added with n-hexane, and the resulting solution was washed with, in turn, water and a saturated aqueous sodium chloride solution and dried over magnesium sulfate. The solvent was evaporated under reduced pressure to give 4.3 g of the glassy title compound.
Mass(EI); m/z: 1030(M$^+$)
PMR(CDCl$_3$)
δ (ppm)=0.10(2'-O-TMS), 0.15(4"-O-TMS), 2.22[3'-N(CH$_3$)$_2$], 3.02(6-OCH$_3$), 3.32(3"-OCH$_3$)

EXAMPLE 12

Preparation of 2',4"-O-bis(trimethylsilyl) erythromycin A 9-[O-(o-chlorobenzyl)oxime] from erhtyromycin A 9-[O-(o-chlorobenzyl)oxime]

To a solution of 15.27 g of erythromycin A 9-[O-(o-chlorobenzyl)oxime], obtained in Example 11(1), in 150 ml of N,N-dimethylformamide were added 7.8 ml of 1,1,1,3,3,3-hexamethyldisilazane and 2.6 g of pyridine hydrochloride, and the mixture was stirred at room temperature for 3 hours. The reaction solution was poured into water and extracted with ethyl acetate, and the extract was washed with, in turn, water and a saturated aqueous sodium chloride solution and dried over anhydrous magnesium sulfate. The solvent was evaporated under reduced pressure to give 14.5 g of the title compound, which was identical with the compound obtained in Example 11(2) in terms of spectra of mass and PMR.

EXAMPLE 13

Preparation of 2',4"-O-bis(trimethylsilyl) erythromycin A 9-[O-(o-chlorobenzyl)oxime] from erythromycin A 9-oxime To a solution of 3 g of erythromycin A 9-oxime in 15 ml of N,N-dimethylformamide were added 0.773 g of o-chlorobenzyl chloride and 0.192 g of 60% sodium hydride, and the mixture was stirred under ice-cooling for 2 hours. After completion of the reaction, the mixture was armed to room temperature. To the reaction mixture were added 1.69 ml of 1,1,1,3,3,3-hexamethyldisilazane and 0.321 g of ammonium chloride, and the mixture was stirred at room temperature for 20 hours. To the reaction solution were added 50 ml of n-hexane and 100 ml of a saturated aqueous sodium chloride solution, and the organic layer was washed with a saturated aqueous sodium chloride solution (100 ml×2) and dried over anhydrous magnesium sulfate. The solvent was evaporated under reduced pressure to give 4.2 g of the title compound, which was identical with the compound obtained in Example 11(2) in terms of spectra of mass and PMR.

Referential Example 1

Preparation of 6-O-methylerythromycin A from 2',4"-O-bis(trimethylsilyl)-6-O-methylerythromycin A 9-(O-allyloxime)

To a solution of 10.3 g of crude 2',4"-O-bis-(trimethylsilyl)-6-O-methylerythromycin A 9-(O-allyloxime), obtained in Example 9, in 100 ml of methanol was added 6.2 ml of 99% formic acid, and the mixture was stirred at 50° C. for an hour. To the reaction solution was added 300 ml of water, and the mixture was made basic with 2N aqueous sodium hydroxide solution and extracted with ethyl acetate. The organic layer was washed with a saturated aqueous sodium chloride solution and dried over anhydrous magnesium sulfate. The solvent was evaporated to give 8.93 g of crude 6-O-methylerythromycin A 9-(O-allyloxime).

To a solution of 8.93 g of crude 6-O-methylerythromycin A 9-(O-allyloxime), obtained above, in a mixture of 50 ml of dioxane and 7.5 ml of water were added 89 mg of palladium acetate, 539 mg of triphenyl phosphine and 9.7 g of triethylammonium formate, and the mixture was refluxed for 30 minutes. After completion of the reaction, the solvent was evaporated under reduced pressure, 200 ml of diethyl ether was added, and the mixture was extracted with 10% acetic acid. The acetic acid layer was washed with, in turn, diethyl ether and n-hexane, made basic with 5N-sodium hydroxide and extracted with ethyl acetate. The organic layer was washed with a saturated aqueous sodium chloride solution and dried over anhydrous magnesium sulfate, and the solvent was evaporated to give 8.5 g of crude 6-O-methylerythromycin A 9-oxime.

To a solution of 8.5 g of 6-O-methylerythromycin A 9-oxime, obtained above, in a mixture of 40 ml of ethanol and 40 ml of water were added 4.65 g of sodium hydrogen sulfite and 1 ml of 99% formic acid, and the mixture was refluxed for 100 minutes. To the reaction solution was added 130 ml of water, and the mixture was adjusted to pH about 9.5 with an aqueous sodium hydroxide solution and stirred under ice-cooling for an hour. The resulting precipitate was collected by filtration, washed throughly with water, and recrystallized from ethanol to give 4.19 g of 6-O-methylerhtyromycin A.

m.p. 223–225° C.

Referential Example 2

Preparation of 6-O-methylerythromycin A from 2', 4"-O-bis(trimethylsilyl)-6-O-methylerythromycin A 9-[O-(o-chlorobenzyl)oxime]

To a solution of 2.8 g of crude 2,4"-O-bis(trimethylsilyl)-6-O-methylerythromycin A 9-[O-(o-chlorobenzyl)oxime], obtained in Example 12, in 30 ml of methanol were added 450 mg of 10% palladium carbon, 1.8 ml of formic acid and 300 mg of ammonium formate, and the mixture was stirred at 60° C. for 2 hours. The palladium catalyst was filtered off, and the filtrate, after addition of 200 ml of water, was made basic with 2N aqueous sodium hydroxide solution. The precipitate which formed was collected by filtration, washed with water and dried to give 1.7 g of crude 6-O-erythromycin A 9-oxime.

By reacting 6-O-erythromycin A 9-oxime thus obtained with sodium hydrogen sulfite and 99% formic acid according to the procedure similar to that of Referential EXAMPLE 1, there was obtained 1.17 g of 6-O-methylerythromycin A as crystals.

m.p. 223–225° C.

What is claimed is:

1. A process for preparing a 6-O-methylerythromycin A derivative represented by the formula:

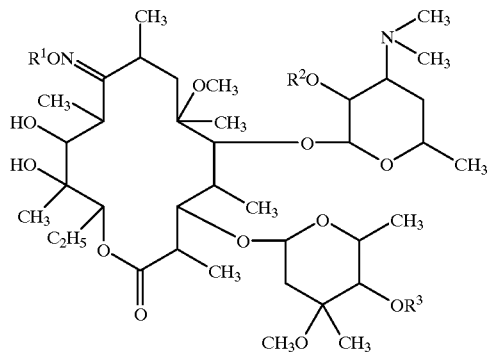

wherein $R^1$ is:
   a 2-alkenyl group having 3 to 15 carbon atoms,
   a benzyl group, or
   a benzyl group substitued by 1 to 3 of a chlorine atom, an alkoxy group having 1 to 4 carbon atoms, a nitro group or an alkoxycarbonyl group having 2 to 6 carbon atoms, and
$R^2$ and $R^3$ are trimethylsilyl,
which comprises reacting, in any desired sequence, erythromycin A 9-oxime with a compound of formula $R^1$—X (wherein $R^1$ is as defined above, and X is a halogen atom) and with a substituted silylating agent having $R^2$ group to give a compound represented by the formula;

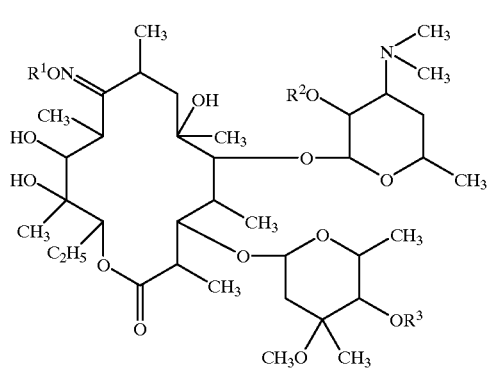

(wherein $R^1$, $R^2$ and $R^3$ are as defined above), and then reacting said compound of formula II with a methylating agent selected from the group consisting of methyl bromide, methyl iodide, dimethyl sulfate, methyl p-toluene sulfonate and methyl methane sulfonate, the amount said methylating agent being 1–3 molar equivalents of said compound of formula II, said trimethylsilyl group ($R^2$) protecting the 2' hydroxyl group against methylation and the 3'-dimethylamino group from being quaternized with the methylating agent.

* * * * *

UNITED STATES PATENT AND TRADEMARK OFFICE
CERTIFICATE OF CORRECTION

PATENT NO. : 6,342,590 B1
DATED : January 29, 2001
INVENTOR(S) : Morimoto et al.

It is certified that error appears in the above-identified patent and that said Letters Patent is hereby corrected as shown below:

<u>Column 4,</u>
Line 54, "41-positions" should read -- 4"-positions --

<u>Column 12,</u>
Line 54, after "and" insert -- preventing --

Signed and Sealed this

Second Day of July, 2002

*Attest:*

JAMES E. ROGAN
*Attesting Officer*     *Director of the United States Patent and Trademark Office*